US008153990B2

(12) United States Patent
Saito

(10) Patent No.: US 8,153,990 B2
(45) Date of Patent: Apr. 10, 2012

(54) PARTICLE BEAM THERAPY SYSTEM

(75) Inventor: Kazuyoshi Saito, Hitachi (JP)

(73) Assignee: Hitachi, Ltd., Tokyo (JP)

( * ) Notice: Subject to any disclaimer, the term of this patent is extended or adjusted under 35 U.S.C. 154(b) by 42 days.

(21) Appl. No.: 12/427,011

(22) Filed: Apr. 21, 2009

(65) Prior Publication Data

US 2009/0289194 A1 Nov. 26, 2009

(30) Foreign Application Priority Data

May 20, 2008 (JP) ................................ 2008-131463

(51) Int. Cl.
*A61N 5/00* (2006.01)

(52) U.S. Cl. ............... 250/396 R; 250/492.1; 250/492.3

(58) Field of Classification Search ............... 250/492.1, 250/492.3, 396 R, 396 ML; 315/500–507
See application file for complete search history.

(56) References Cited

U.S. PATENT DOCUMENTS 4,870,287 A * 9/1989 Cole et al. .................. 250/492.3
5,260,581 A * 11/1993 Lesyna et al. .............. 250/492.3
5,363,008 A * 11/1994 Hiramoto et al. ............... 313/62
6,476,403 B1 11/2002 Dolinskii et al.
7,102,144 B2 * 9/2006 Matsuda et al. ........... 250/492.1
7,122,978 B2 * 10/2006 Nakanishi et al. ............ 315/500
7,465,944 B2 * 12/2008 Ueno et al. ................. 250/492.3
2005/0231138 A1 * 10/2005 Nakanishi et al. ............ 315/500
2009/0065706 A1 * 3/2009 Saito et al. ............. 250/396 ML
2009/0114852 A1 * 5/2009 Saito et al. .................. 250/492.3
2009/0184263 A1 * 7/2009 Moriyama et al. ......... 250/492.3

FOREIGN PATENT DOCUMENTS

EP 1 584 353 A1 10/2005
JP 1-286300 A 11/1989
JP 2005-332794 A 12/2005

OTHER PUBLICATIONS

Unpublished U.S. Appl. No. 12/252,448, filed Oct. 16, 2008.
T. Furukawa et al., “Characteristics of fast beam switching for spot scanning”, Nuclear Instruments & Methods in Physics Research, Nov. 15, 2002, 11 pp., vol. 503.

* cited by examiner

*Primary Examiner* — Michael Maskell
(74) *Attorney, Agent, or Firm* — Mattingly & Malur, PC

(57) ABSTRACT

A particle beam therapy system that is capable of irradiating a target area with an irradiation beam suitable for a particle beam therapy using a spot scanning method includes a synchrotron, a beam transport system and an irradiation device. The beam transport system is provided with a beam interrupting device adapted to block supply of a charged particle beam to the irradiation device. The beam interrupting device has a beam shielding magnet, an exciting power supply for the beam shielding magnet and a beam dump. The beam transport system has a bending magnet. The beam shielding magnet is provided on an inlet side of the bending magnet. The beam dump is provided on an outlet side of the bending magnet. A controller controls the exciting power supply to control the timing of an operation of the beam shielding magnet.

11 Claims, 11 Drawing Sheets

PARTICLE BEAM THERAPY SYSTEM

BACKGROUND OF THE INVENTION

1. Field of the Invention

The present invention relates to a particle beam therapy system capable of high precision irradiation for treatment, and more particularly to a particle beam therapy system suitable for using a spot scanning irradiation method.

2. Description of the Related Art

In the recent aging society, a typical one of radiation therapies has attracted attention as one of cancer treatments since the radiation therapy is noninvasive to and has a low impact on human bodies. In addition, after the radiation therapy, the quality of life is highly maintained. Among the radiation therapies, a particle beam therapy system is a promising approach since the system provides an excellent dose concentration for an affected area of a patient. The particle beam therapy system uses a proton or a charged particle beam such as carbon, which is accelerated by an accelerator. The particle beam therapy system includes an accelerator, a beam transport system and an irradiation device. The accelerator such as a synchrotron or cyclotron is adapted to accelerate a beam emitted by an ion source to a level close to the speed of light. The beam transport system is adapted to transport the beam extracted from the accelerator. The irradiation device is adapted to irradiate an affected area of a patient with the beam in accordance with the location and shape of the affected area.

Conventionally, in an irradiation device provided in a particle beam therapy system, a beam is formed by increasing the diameter of the beam by a scatterer and removing an outer periphery of the beam by a collimator in order to irradiate an affected area of a patient with the beam in accordance with the shape of the affected area. In this conventional method, the efficiency of using the beam is low, and unnecessary neutrons tend to be generated. In addition, there is a limitation in matching the shape of the beam with the shape of an affected area of a patient. Recently, there has been an increased need for a scanning irradiation method as a higher precision irradiation method. In the scanning irradiation method, a beam having a small diameter is extracted from an accelerator, and bent by an electromagnet. An affected area of a patient is then scanned by the beam in accordance with the shape of the affected area.

In the scanning irradiation method, a three-dimensional shape of an affected area is divided into a plurality of layers in a depth direction, and each of the layers is two-dimensionally divided into a plurality of portions to set a plurality of irradiation spots. Each of the layers is selectively irradiated with an irradiation beam by adjusting the energy of the irradiation beam in accordance with the depth position of the layer. Each of the layers is two-dimensionally scanned with the irradiation beam by electromagnets. Each irradiation spot is irradiated with the irradiation beam with a predetermined dose. A method for continuously turning on an irradiation beam while the beam spot is moved from an irradiation spot to another irradiation spot is called raster scanning, whereas a method for turning off an irradiation beam while the beam spot is moved from an irradiation spot to another irradiation spot is called spot scanning.

In the conventional spot scanning method, each irradiation spot is irradiated with a beam with a predetermined dose under the condition that beam scanning is stopped, and after the irradiation beam is turned off, the amount of an exciting current flowing in a scanning magnet is adjusted, and then the beam spot is moved to the location of the next irradiation spot. To achieve high precision irradiation for treatment using the spot scanning method, it is necessary to position a spot of an irradiation beam with high accuracy and to turn on and off the irradiation beam at a high speed. Especially, it is necessary to turn off the irradiation beam at a high speed.

To obtain high accuracy of positioning of the irradiation beam spot, a known beam extraction method is used. In the beam extraction method, the size of the circulating beam is increased by a radio-frequency power, and particles having large amplitude and exceeding a stability limit are extracted in order to extract a beam from a synchrotron. In this method, since an operation parameter of an extraction related apparatus for the synchrotron can be set to be constant during the extraction of the particle, orbit stability of the extracted beam is high. Therefore, an irradiation beam can be positioned with high accuracy, which is required for the spot scanning method.

However, it takes a certain time to block the extracted beam after radio-frequency (RF) power for extraction is turned off at the time of termination of irradiation on each spot. Thus, the irradiation during the delay time (delayed irradiation) occurs. It is necessary to reduce the irradiation dose of the delayed extracted beam in the spot scanning method in order to maintain the accuracy of the irradiation dose. Therefore, the beam extracted from the synchrotron is controlled to prevent the beam from reaching an irradiation device by turning on and off a shielding magnet provided in a beam transport system during a movement of the beam spot from an irradiation spot to another irradiation spot. For example, JP-A-2005-332794 discloses that an extracted beam is deflected by a shielding magnet provided in a straight section of a beam transport system and an unnecessary component (that may cause delay irradiation) of the beam is removed by a beam dump provided on the downstream side of the straight section of the beam transport system. FIG. 11 shows the configuration of a conventional particle beam therapy system having a beam interrupting device.

On the other hand, when the cyclotron is used as the accelerator, delayed irradiation may occur. A voltage applied to an ion source is controlled to turn on and off a beam that is to be extracted from the cyclotron. After the application of the voltage to the ion source is stopped upon termination of irradiation on each spot, it takes a certain time to block the beam in order to prevent the beam from being extracted from the cyclotron. To take measures for the above problem, for example, JP-A-2005-332794 discloses a particle beam therapy system (shown in FIG. 11) having a synchrotron, as is the case with a synchrotron used as the accelerator.

SUMMARY OF THE INVENTION

It is, however, difficult to reduce a time for blocking a beam in order to prevent the beam from being extracted from the accelerator in the conventional technique described in JP-A-2005-332794. This is because an exciting power supply used for the system needs to supply a high voltage and a large current and is therefore expensive. In addition, a shielding magnet used for the system needs to be large in size to enhance voltage resistance characteristics and thermal cooling resistance characteristics. In order to reduce the required performance of the shielding magnet and the required performance of the exciting power supply, the drift length of the straight section of a beam transport system provided between the shielding magnet and a beam dump is increased. This leads to an increase in the size of the system and results in difficulty in adjusting beam transportation.

It is an object of the present invention to provide a particle beam therapy system that is capable of irradiating a target area with an irradiation beam suitable for a particle beam therapy using a spot scanning method and that can be constructed in a small size, with low cost and being easily adjusted.

In order to accomplish the abovementioned object, a particle beam therapy system according to an aspect of the present invention comprises: an accelerator for accelerating a charged particle beam such that the charged particle beam has a predetermined energy level to be extracted; an irradiation device for irradiating a target area with the charged particle beam; a beam transport system having a bending magnet and adapted to introduce the charged particle beam extracted from the accelerator into the irradiation device, the bending magnet being adapted to bend the charged particle beam; and a beam interrupting device provided in the beam transport system and adapted to block supply of the charged particle beam to the irradiation device; wherein the beam interrupting device includes a beam shielding magnet and a beam dump, the beam shielding magnet being located on an upstream side of the bending magnet with respect to the direction of flow of the charged particle beam, the beam dump being located on a downstream side of the bending magnet with respect to the direction of the flow of the charged particle beam or located in the bending magnet.

According to another aspect of the present invention, the particle beam therapy system further comprises a quadrupole magnet provided between the bending magnet and the beam shielding magnet and adapted to bend the charged particle beam bent by the beam shielding magnet, the bending magnet constituting a part of the beam transport system, the beam shielding magnet being located on an inlet side of the bending magnet.

According to still another aspect of the present invention, when the bending magnet included in the beam transport system is configured as a rectangular type and opposed end surfaces substantially parallel to each other, the beam shielding magnet is adapted to bend the charged particle beam to cause the charged particle beam to propagate in a bending plane of the bending magnet.

According to still another aspect of the present invention, when the bending magnet included in the beam transport system is configured as a sector type, the beam shielding magnet is adapted to bend the charged particle beam to cause the charged particle beam to propagate in a direction perpendicular to a bending plane of the bending magnet.

According to the present invention, since a space in which the bending magnet included in the beam transport system is provided can be used as a drift space, a compact particle beam therapy system can be provided.

DESCRIPTION OF THE PREFERRED EMBODIMENTS

First Embodiment

The configuration and operations of a particle beam therapy system according to a first embodiment of the present invention are described below with reference to FIGS. 1 to 4E.

Figure 1:
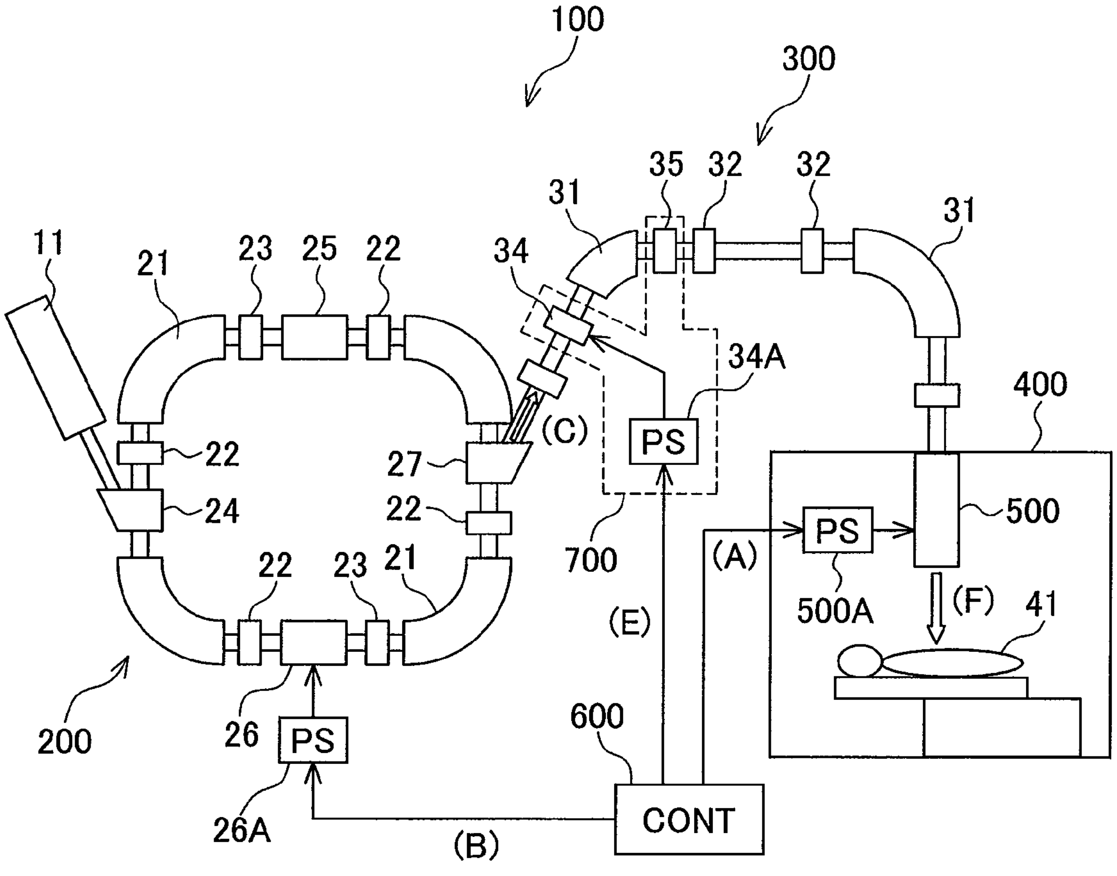
FIG. 1 is a diagram showing the configuration of a particle beam therapy system according to a first embodiment of the present invention.

First, a description will be made of the entire configuration of the particle beam therapy system according to the first embodiment and the principle of irradiation with a particle beam with reference to FIGS. 1 to 3B. FIG. 1 is a diagram showing the configuration of the particle beam therapy system according to the first embodiment.

In FIG. 1, reference numeral 100 denotes the particle beam therapy system. The particle beam therapy system 100 includes a synchrotron 200, a beam transport system 300, an irradiation device 500 and a controller 600. The synchrotron 200 is adapted to accelerate a charged particle beam pre-accelerated by a pre-accelerator 11 such as a linac such that the charged particle beam has a predetermined energy level and then to output the charged particle beam. The beam transport system 300 is adapted to introduce the charged particle beam extracted from the synchrotron 200 into a treatment room 400. The irradiation device 500 is adapted to irradiate an affected area of a patient 41 with the charged particle beam in accordance with the shape of the affected area in the treatment room.

The synchrotron 200 includes an injection device 24, bending magnets 21, quadrupole magnets 22, sextupole magnets 23, an accelerating cavity 25, an extraction device 26, a power supply 26A and an extraction deflecting magnet 27. The injection device 24 is adapted to receive a charged particle beam pre-accelerated by the pre-accelerator 11. The bending magnets 21 are adapted to bend the charged particle beam in order to cause the charged particle beam to circulate on a constant orbit. The quadrupole magnets 22 are focus/defocus type adapted to apply focusing forces directed in horizontal and vertical directions to the charged particle beam to prevent the charged particle beam from spreading. The accelerating cavity 25 is adapted to accelerate the charged particle beam by a radio-frequency accelerating voltage such that the charged particle beam has a predetermined energy level. Each of the sextupole magnets 23 is adapted to define a stability limit for oscillation amplitude of the circulating charged particle beam. The extraction device 26 is adapted to increase the oscillation amplitude of the charged particle beam by a radio-frequency electromagnetic field, cause the charged particle beam to exceed the stability limit, and cause the charged particle beam to be extracted from the synchrotron 200. The power supply 26A is adapted to supply radio-frequency (RF) power for extraction to the extraction device 26. The extraction deflecting magnet 27 is adapted to bend the charged particle beam in order to cause the charged particle beam to be extracted from the synchrotron 200.

A description will be made of a method for extracting a charged particle beam from the synchrotron 200 provided in the particle beam therapy system 100 according to the first embodiment with reference to FIGS. 2A and 2B.

Figure 2A:
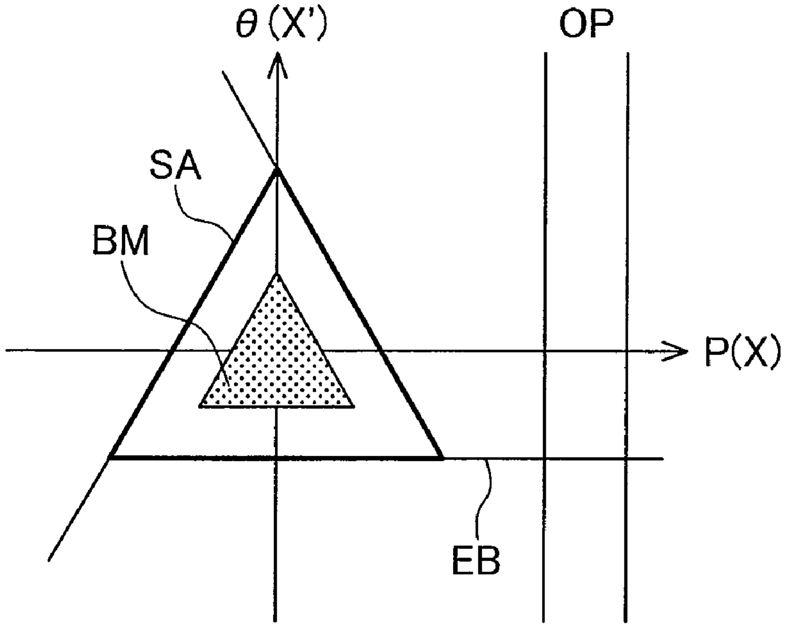
FIGS. 2A and 2B are diagrams each showing a method for extracting a charged particle beam from a synchrotron provided in the particle beam therapy system according to the first embodiment.
Figure 2B:
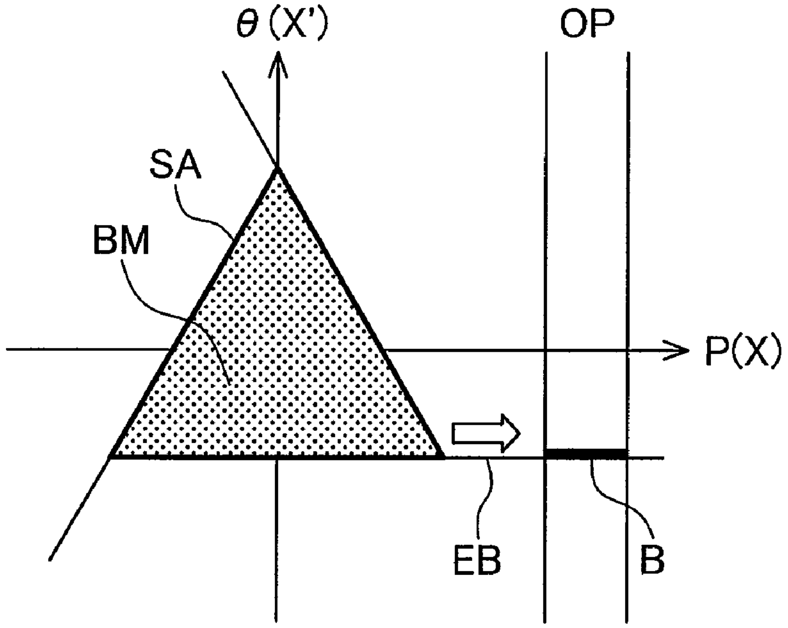

FIGS. 2A and 2B are explanatory diagrams each showing the method for extracting a charged particle beam from the synchrotron 200 provided in the particle beam therapy system 100 according to the first embodiment.

Each of FIGS. 2A and 2B shows the state of the charged particle beam circulating in the synchrotron 200 within a phase space in the horizontal direction, which is related to the extraction. In each of FIGS. 2A and 2B, an abscissa axis indicates the position (P) of the charged particle beam shifted from a design orbit, and an ordinate axis indicates an inclination (angle θ) with respect to the design orbit. FIG. 2A shows the phase space in the horizontal direction before the start of the extraction. FIG. 2B shows the phase space in the horizontal direction after the start of the extraction.

As shown in FIG. 2A, each of the particles constituting the charged particle beam oscillates in the horizontal direction and the vertical direction and circulates as a circulating beam BM around the design orbit. A triangle-shaped stable area SA is formed in the phase space by exciting the sextupole magnets 23 shown in FIG. 1. A particle present in the stable area SA continues to stably circulate in the synchrotron 200.

In this case, when radio-frequency power for extraction is applied to the extraction device 26 shown in FIG. 1, the amplitude of the circulating beam BM is increased as shown in FIG. 2B. Oscillation amplitude of a particle extracted from the stable area SA is rapidly increased along an extraction branch EB. The particle extracted from the stable area SA finally enters an opening portion OP of the extraction deflecting magnet 27 and is extracted from the synchrotron 200 as an extracted beam B.

The size of the stable area SA is determined based on the amount of an exciting current flowing in the quadrupole magnets 22 or in the sextupole magnets 23. FIG. 2A shows the phase space before the start of the extraction. FIG. 2B shows the phase space after the start of the extraction. The size of the stable area SA is set to be larger than emittance (which is an extent occupied by particles of the charged particle beam in the phase space) of the charged particle beam before the start of the extraction. To extract the charged particle beam from the synchrotron 200, at the time of starting of the extraction, a radio-frequency electromagnetic field for the extraction is applied to the extraction device 26. The emittance of the charged particle beam then becomes large (the oscillation amplitudes of the particles are increased), and a particle exceeding the stability limit is extracted from the synchrotron 200. Under this condition, by turning on and off the radio-frequency electromagnetic field for the extraction, the extracted beam can be controlled to be turned on and off. In this extraction method, the amount of the exciting current flowing in the magnet is constant during the extraction, and the stable area and the extraction branch are not varied. Therefore, the position and size of the spot of the extracted beam are stable. An irradiation beam suitable for the scanning method can be achieved.

Referring back to FIG. 1, the beam transport system 300 includes bending magnets 31, focus/defocus type quadrupole magnets 32 and a beam interrupting device 700. The bending magnets 31 are adapted to bend the charged particle beam extracted from the synchrotron 200 by a magnetic field and introduce the charged particle beam into the treatment room 400 along a predetermined design orbit. The focus/defocus type quadrupole magnets 32 are adapted to apply focusing forces directed in the horizontal and vertical directions to the charged particle beam to prevent the charged particle beam from spreading during the transport of the charged particle beam. The beam interrupting device 700 is adapted to turn on and off the supply of the charged particle beam to the irradiation device 500 provided in the treatment room 400.

The beam interrupting device 700 includes a beam shielding magnet 34, an exciting power supply 34A and a beam dump 35. The exciting power supply 34A is provided for the beam shielding magnet 34. The beam dump 35 is adapted to discard a beam component removed by the beam shielding magnet 34. The exciting power supply 34A is connected with the beam shielding magnet 34. The controller 600 is connected with the exciting power supply 34A and adapted to control excitation of the beam shielding magnet 34. The beam shielding magnet 34, the bending magnet 31, the beam dump 35 and the quadrupole magnet 32 are arranged in the beam transport system 300 in order from the upstream side of the flow of the charged particle beam. In the present embodiment, the bending magnet 31 is separately provided from the beam dump 35. The beam dump 35 may be provided in the bending magnet 31, and the core of the bending magnet 31 may serve a radiation shielding function. The bending magnet 31 is separately provided from the beam dump 35 to improve maintainability.

As a method for turning on and off the charged particle beam to be supplied to the irradiation device 500 by the beam interrupting device 700, there are two methods. In one method, the beam shielding magnet 34 may bend an unnecessary beam component by a dipole magnetic field generated when the beam shielding magnet 34 is excited, so as to discard the unnecessary beam component by the beam dump 35. In another method, the beam shielding magnet 34 may bend a beam component by the dipole magnetic field generated when the beam shielding magnet 34 is excited, so as to supply only the beam component to the irradiation device 500. In the former method, the bending magnet 34 bends the unnecessary component of the charged particle beam extracted from the synchrotron 200 and causes the unnecessary beam component to collide with the beam dump 35. In the latter method, the excitation of the beam shielding magnet 34 is stopped to cause the unnecessary beam component to collide with the beam dump 35 and to thereby stop the supply of the charged particle beam to the irradiation device 500. In the former method, the beam transport system 300 can be easily adjusted. In the latter method, since the particle beam therapy system can block the supply of the charged particle beam to the irradiation device 500 without controlling any device included in the particle beam therapy system during a failure of a device included in the beam interrupting device, the particle beam therapy system is highly secure. Although both of the methods can be performed in the system, the former method is described in the present embodiment.

Figure 3A:
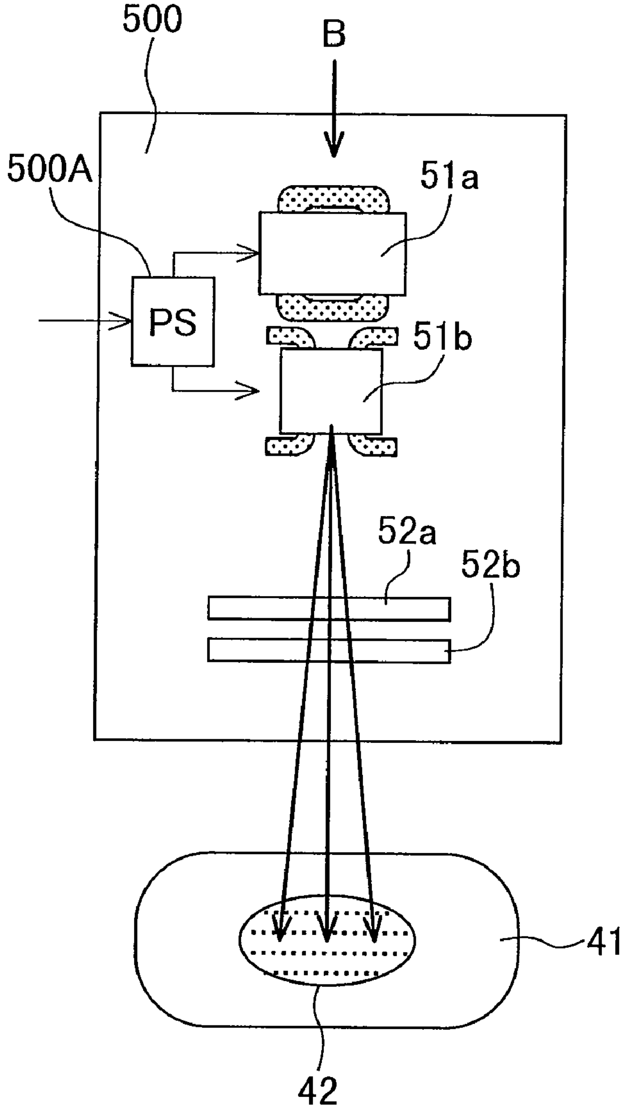
FIG. 3A is a front view of an irradiation device used in the particle beam therapy system according to the first embodiment.

The irradiation device 500 has a power supply 500A for scanning magnets 51*a* and 51*b*. The configuration of the irradiation device 500 used in the particle beam therapy system 100 according to the present embodiment is described with reference to FIGS. 3A and 3B. FIG. 3A is a front view of the irradiation device 500 used in the particle beam therapy system 100 according to the first embodiment of the present invention.

The irradiation device 500 includes the scanning magnets 51*a* and 51*b*, the power supply 500A, and beam monitors 52*a* and 52*b*. The scanning magnets 51*a* and 51*b* are adapted to bend the charged particle beam introduced from the beam transport system 300 in the horizontal and vertical directions in order to two-dimensionally scan the charged particle beam in conformity with the cross sectional shape of an affected area 42 of the patient 41. The power supply 500A is connected with the scanning magnets 51*a* and 51*b* and provided for the scanning magnets 51*a* and 51*b*. The beam monitors 52*a* and 52*b* are adapted to monitor the position, size (shape) and dose of the charged particle beam.

As shown in FIG. 1, the controller 600 is connected with the power supply 26A, the exciting power supply 34A and the power supply 500A. The power supply 26A is provided for the extraction device 26 included in the synchrotron 200. The power supply 34A is provided for the beam shielding magnet 34 included in the beam interrupting device 700. The power supply 500A is provided for the scanning magnets 51*a* and 52*b* included in the irradiation device 500. The controller 600 transmits an extraction RF control signal to the power supply 26A to turn on and off a RF magnetic field that is to be applied to the extraction device 26. In addition, the controller 600 transmits a beam shielding control signal to the power supply 34A to control turn on and off of the beam shielding magnet 34 (amount of exciting current). Furthermore, the controller 600 transmits a scanning command signal to the power supply 500A to control the scanning magnets 51*a* and 51*b*.

Figure 3B:
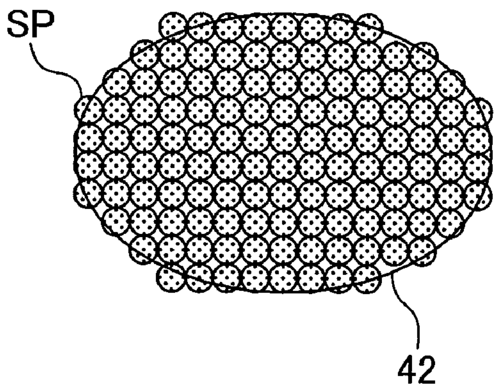
FIG. 3B is a diagram showing an affected area of a patient when viewed from the upstream side of flow of an irradiation beam.

The spot scanning method is described below with reference to FIGS. 3A and 3B. FIG. 3B is a diagram showing the affected area 42 of the patient 41 when viewed from the upstream side of flow of an irradiation beam.

As shown in FIG. 3A, the affected area 42 of the patient 41 is divided into a plurality of layers in a three-dimensional depth direction. Each of the layers is divided into a plurality of portions two-dimensionally to set a plurality of irradiation spots. Each of the layers located at depth positions different from each other is selectively irradiated with the irradiation beam by adjusting the energy level of the beam extracted from the synchrotron 200 and thereby changing the energy level of the irradiation beam. As shown in FIG. 3B, the scanning magnet 51*a* or 51*b* (the scanning magnets 51*a* and 51*b* are collectively referred to as the scanning magnet 51) bends the irradiation beam (to be used for scanning) such that the irradiation device irradiates irradiation spots SP present on each of the layers with the irradiation beam with respective predetermined doses. In this case, after the predetermined dose of the irradiation beam is provided to one of the irradiation spots SP, the irradiation beam is blocked at a high speed. After that, the beam spot is moved to the location of another irradiation spot under the condition that the irradiation beam is turned off, and the irradiation is progressed in this way to perform the spot scanning method. Before the beam spot is moved to the location of the other irradiation spot, the controller 600 controls the beam interrupting device 700 such that the beam interrupting device 700 blocks supply of the charged particle beam to the irradiation device 500.

The operations performed in accordance with the spot scanning method by the particle beam therapy system 100 according to the present embodiment are described with reference to FIGS. 4A to 4E. FIGS. 4A to 4E are timing charts of the operations performed in accordance with the spot scanning method by the particle beam therapy system 100 according to the present embodiment.

In FIGS. 4A to 4E, each of the abscissa axes indicates a time t. An ordinate axis of the timing chart shown in FIG. 4A indicates the amount of a current supplied to the scanning magnet 51 from the power supply 500A in response to a scanning command signal supplied from the controller 600 to the power supply 500A provided for the scanning magnet 51. An ordinate axis of the timing chart shown in FIG. 4B indicates the extraction RF power supplied to the extraction device 26 from the power supply 26A in response to an extraction RF control signal supplied from the controller 600 to the power supply 26A provided for the extraction device 26. An ordinate axis of the timing chart shown in FIG. 4C indicates the on and off states of a beam extracted from the synchrotron 200 to the beam transport system 300. An ordinate axis of the timing chart shown in FIG. 4D indicates the on and off states of an exciting current supplied from the power supply 34A to the beam shielding magnet 34 in response to a beam shielding control signal supplied from the controller 600 to the power supply 34A provided for the beam shielding magnet 34. An ordinate axis of the timing chart shown in FIG. 4E indicates the on and off states of the beam output from the irradiation device 500. When the irradiation beam is in the on state, spots S1, S2, S3 and S4 are formed.

Figures 4A, 4B, 4C, 4D, 4E:
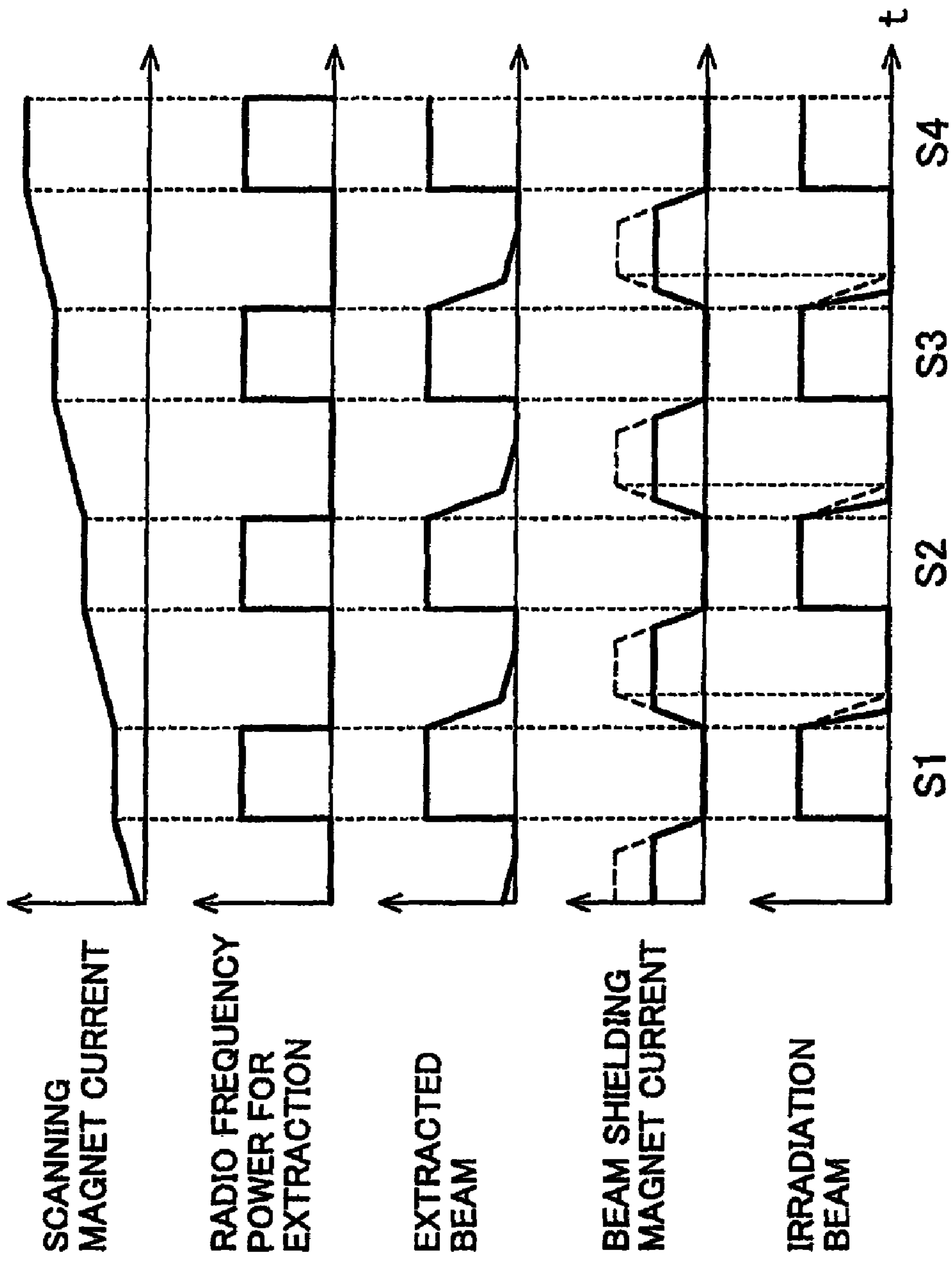
FIGS. 4A to 4E are timing charts showing operations performed in accordance with a spot scanning method used in the particle beam therapy system according to the first embodiment.

As shown in FIG. 4A, an area to be irradiated with the irradiation beam is scanned by increasing the amount of a current that is to be supplied to the scanning magnet 51 from the power supply 500A, and an area to be irradiated with the irradiation beam is specified by maintaining the amount of a current that is to be supplied to the scanning magnet 51 from the power supply 500A. In the spot scanning method, each of the irradiation spots S1, S2 and S3 is irradiated with the irradiation beam with a predetermined dose under the condition that the beam scanning is stopped, and when the dose of the charged particle beam incident on each of the irradiation spots has reached a target irradiation dose (set value), the irradiation beam is turned off. After that, in the spot scanning method, the amount of the exciting current flowing in the scanning magnet 51 is adjusted such that the next irradiation spot is irradiated with the irradiation beam, as shown in FIGS. 4A to 4E.

As shown in FIG. 4B, the radio-frequency electromagnetic field is applied to the extraction device 26 at the time of the spot irradiation in which the charged particle beam is supplied to the irradiation device 500, while the radio-frequency electromagnetic field to be applied to the extraction device 26 is turned off to block the supply of the charged particle beam to the irradiation device 500 to change the irradiation spot to another irradiation spot. To block the supply of the charged particle beam to the irradiation device 500, the beam shielding magnet 34 provided in the beam transport system 300 is excited. This causes the supply of the charged particle beam to be blocked at high speed, as shown in FIG. 4D. Specifically, when the dose of the charged particle beam incident on one of the irradiation spots has reached the target irradiation dose, the controller 600 transmits an extraction stop signal to the synchrotron 200 (specifically to the power supply 26A). The power supply 26A receives the extraction stop signal and then stops applying the RF magnetic field. The controller 600 controls the beam interrupting device 700 such that the beam interrupting device 700 blocks the charged particle beam extracted from the synchrotron 200 after the transmission of the extraction stop signal. In the present embodiment, the controller 600 controls the beam shielding magnet 34 such that the charged particle beam extracted from the synchrotron 200 after the transmission of the extraction stop signal collides with the beam dump 35. This control reduces an irradiation dose of the delayed extracted beam. The timings of turning on and off the RF magnetic field to be applied to the extraction device 26 and the timing of exciting the beam shielding magnet 34 are controlled by the controller 600.

Features of the present embodiment are described in comparison with the aforementioned conventional technique. As shown in FIGS. 4A to 4E, the beam interrupting device 700 needs to be configured that the amount of the exciting current applied to the beam shielding magnet 34 rapidly increases and is then maintained at a constant value for a long time. Especially, when the spots to be irradiated are remote from each other, it may take a long time to direct the irradiation beam from one of the irradiation spots to another one of the irradiation spots. That is, the irradiation beam is turned off for a long time in remote spot irradiation in which the irradiation spots to be irradiated are remotely located. It is, therefore, necessary that the exciting power supply provided for the beam shielding magnet should supply a high voltage and a large current and should have a high duty cycle. Thus, the exciting power supply is expensive. Furthermore, it is necessary that the beam shielding magnet be complicated and large in size in order to enhance voltage resistance characteristics and thermal cooling resistance characteristics. Thus, in order to reduce the required performance of the shielding magnet and the required performance of the exciting power supply, the drift length of the straight section of the beam transport system provided between the shielding magnet and the beam dump can be increased, and whereby a necessary amount of the exciting current can be reduced. This, however, leads to an increase in the size of the system and results in difficulty in adjusting the beam transportation.

According to the present embodiment, the beam shielding magnet 34 is provided on an inlet side of the bending magnet 31 constituting a part of the beam transport system 300, while the beam dump 35 is provided on an outlet side of the bending magnet 31. In other words, the beam shielding magnet 34 is located on the upstream side of the flow of the charged particle beam, while the beam dump 35 is located on the downstream side of the flow of the charged particle beam. Due to this arrangement, the bending magnet 31 can be used as a drift space. Thus, since a long drift length is not required, it is not necessary that the straight section of the beam transport system 300 be large. Without increasing the drift length of the straight section of the beam transport system 300, an unnecessary beam component can be reliably separated from the beam and discarded. In addition, the required performance of the beam shielding magnet 34 (constituting a part of the beam interrupting device 700) and the required performance of the exciting power supply 34A (constituting a part of the beam interrupting device 700) can be reduced. Furthermore, since it is not necessary to increase the drift length of the straight section of the beam transport system 300, it is easy to focus the charged particle beam by the quadrupole magnets 32. Therefore, the difficulty of adjusting the beam transportation can be avoided. In FIGS. 4D and 4E, broken lines indicates values obtained from a conventional technique. According to the technique (indicated by solid lines in FIGS. 4D and 4E) of the present invention, the amount of the exciting current applied to the beam shielding magnet 34 and the time required for blocking the charged particle beam can be reduced.

Second Embodiment

Next, a description is made of the configuration and operations of a particle beam therapy system according to a second embodiment of the present invention. In the second embodiment, only parts different from the configuration and operations of the particle beam therapy system according to the first embodiment are described below.

Figure 5:
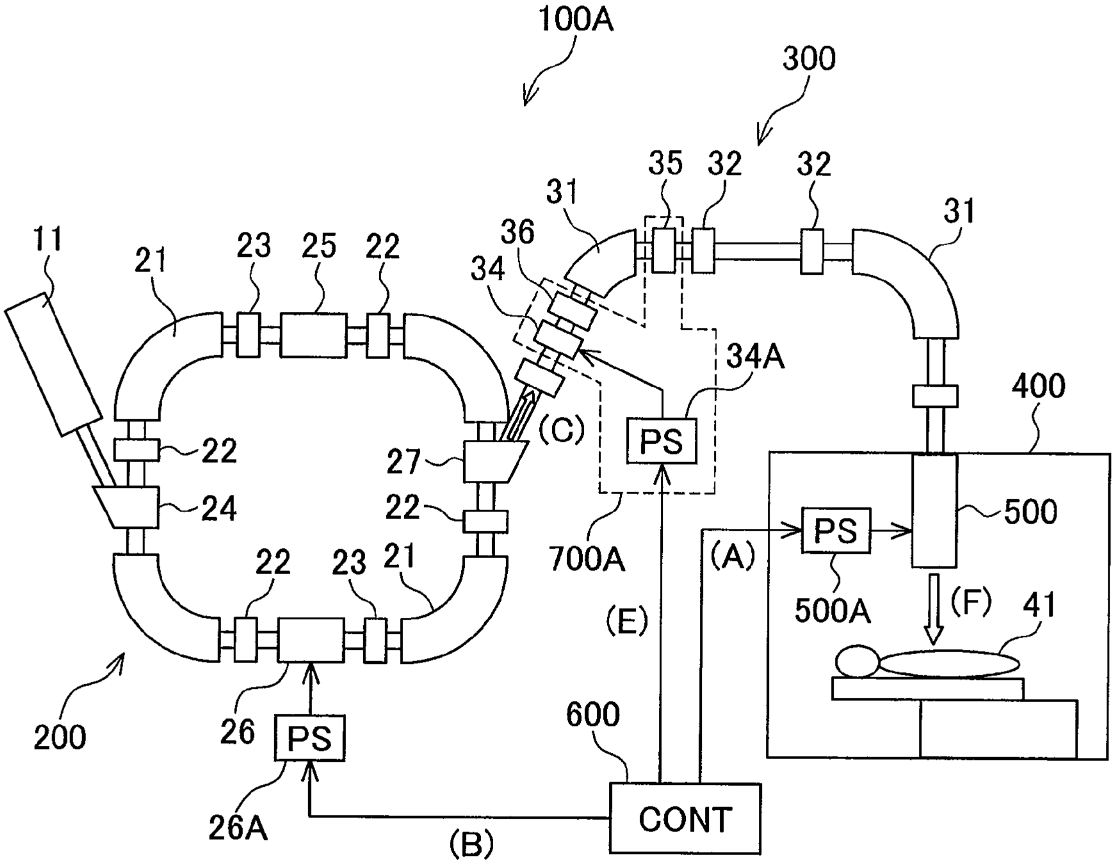
FIG. 5 is a diagram showing the configuration of a particle beam therapy system according to a second embodiment of the present invention.

FIG. 5 is a diagram showing the entire configuration of the particle beam therapy system 100A according to the second embodiment.

The particle beam therapy system 100A has a beam interrupting device 700A. The beam interrupting device 700A includes the beam shielding magnet 34, the exciting power supply 34A, a quadrupole magnet 36 and the beam dump 35. The exciting power supply 34 is adapted to excite the beam shielding magnet 34. The beam dump 35 is adapted to discard a beam component removed from the charged particle beam by the beam shielding magnet 34. The beam shielding magnet 34, the quadrupole magnet 36, the bending magnet 31, the beam dump 35 and the quadrupole magnet 32 are arranged in the beam transport system 300 in order from the upstream side of the flow of the charged particle beam. In the present embodiment, the quadrupole magnet 36 is located between the bending magnet 31 and the beam shielding magnet 34. The bending magnet 31 constitutes a part of the beam transport system 300. The beam shielding magnet 34 is located on the inlet side of the bending magnet 31 and bends the charged particle beam. The quadrupole magnet 36 then further bends the charged particle beam bent by the beam shielding magnet 34. The beam dump 35 located on the outlet side of the bending magnet 31 then discards the charged particle beam bent by the quadrupole magnet 36. The beam dump 35 may be provided in the bending magnet 31, and the core of the bending magnet 31 may serve a radiation shielding function.

Figure 6A:
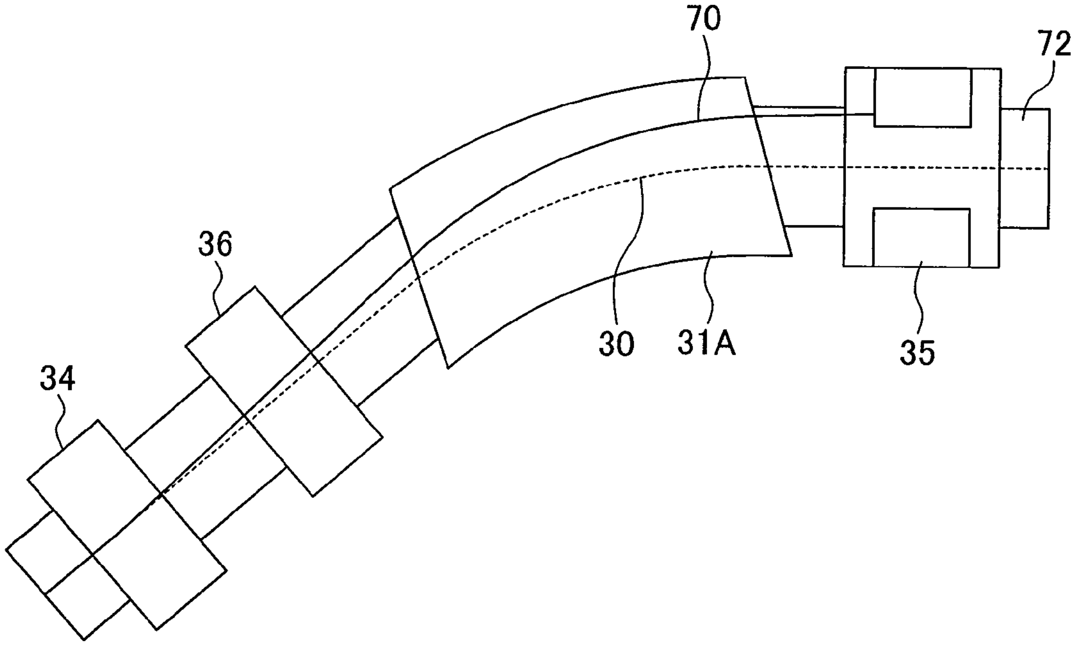
FIGS. 6A and 6B are a first plan view and first front view, respectively, of a beam interrupting device used in the particle beam therapy system according to the second embodiment and show the principle of an operation of the beam interrupting device.
Figure 6B:
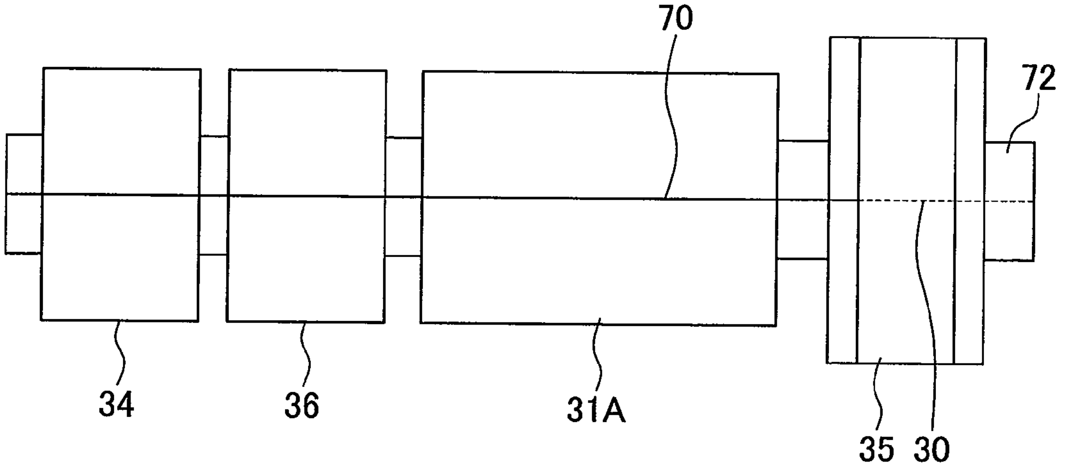

FIGS. 6A and 6B are first diagrams showing the principle of an operation of the beam interrupting device 700A used in the particle beam therapy system 100A according to the second embodiment. In FIGS. 6A and 6B, a bending magnet 31A included in the particle beam therapy system 100A is a rectangular type, and the beam shielding magnet 34 bends the charged particle beam in a bending plane of the bending magnet 31A. Here, the rectangular type means that the opposed surfaces of the magnetic pole, from which the charged particle beam is injected/extracted, are parallel to each other. FIG. 6A is a plan view of the beam interrupting device 700A when viewed from the top of the beam transport system 300. FIG. 6B is a front view of the beam interrupting device 700A when viewed from the side of the beam transport system 300. When the bending magnet 31A of the rectangular type is used, a focusing force acts in a direction perpendicular to the bending plane of the bending magnet 31A to the charged particle beam. However, the charged particle beam does not receive the focusing force in the bending plane. Therefore, the charged particle beam bent at a bending angle (described below) by the beam shielding magnet 34 propagates in the bending magnet 31A under the condition that the bending angle is maintained. In this case, the bending angle is formed between the direction of the propagation of the charged particle beam bent by the beam shielding magnet 34 and an orbit 30 of the charged particle beam in case it is not bent (an orbit of the charged particle beam propagating when the irradiation beam is turned on, which is referred to as a center orbit). In FIGS. 6A and 6B, the charged particle beam receives a diverging force in the bending plane from the quadrupole magnet 36 and then propagates at a larger bending angle with respect to the center orbit 30. Then, the charged particle beam propagates in the bending magnet 31A along an orbit 70 (of the charged particle beam propagating when the irradiation beam is turned off) and is then discarded by the beam dump 35.

Figure 7A:
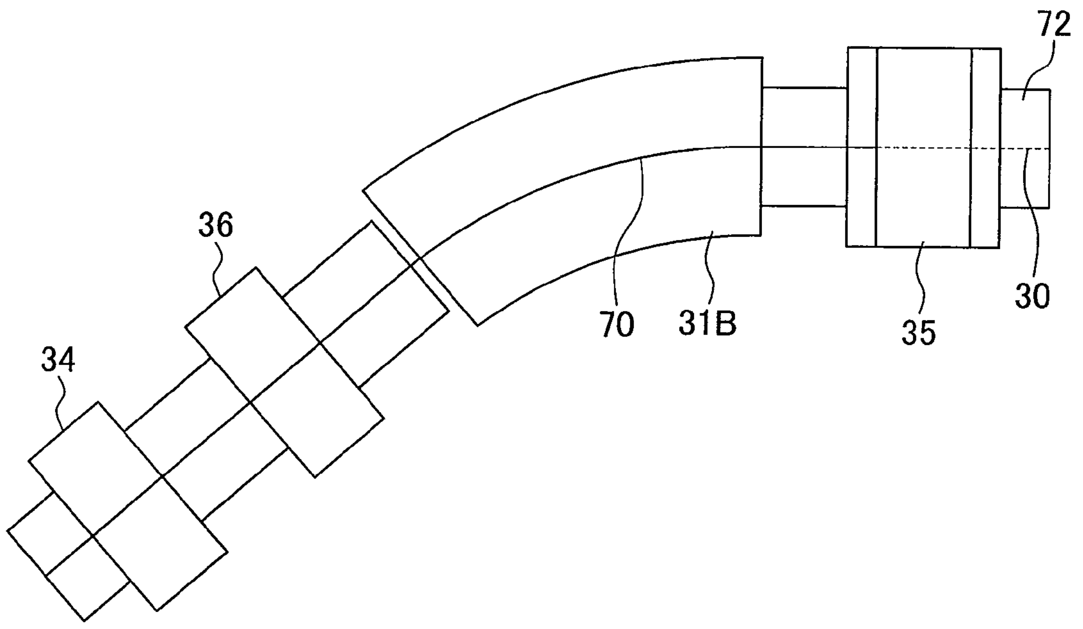
FIGS. 7A and 7B are a second plan view and second front view, respectively, of the beam interrupting device used in the particle beam therapy system according to the second embodiment and show the principle of the operation of the beam interrupting device.
Figure 7B:
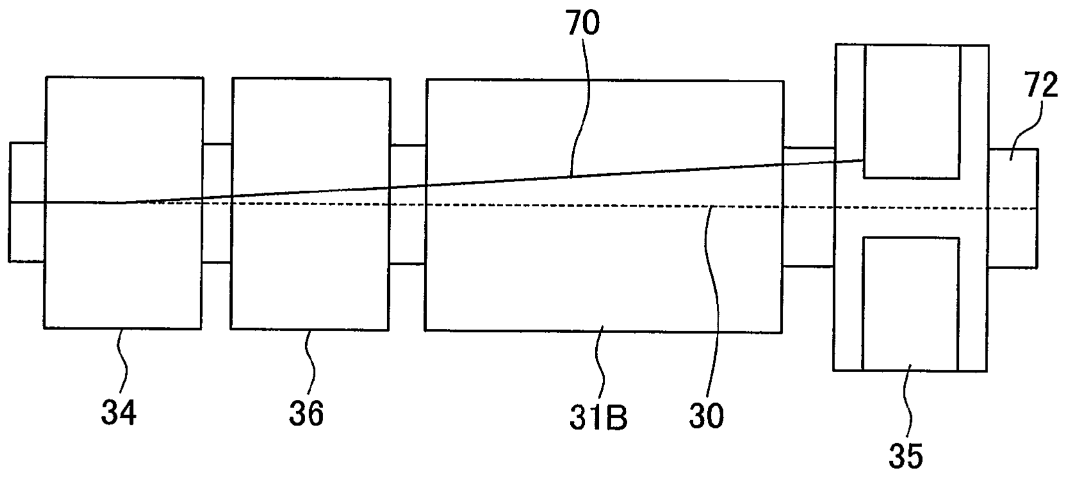

FIGS. 7A and 7B are second diagrams showing the principle of an operation of the beam interrupting device 700A used in the particle beam therapy system 100A according to the second embodiment. The particle beam therapy system 100A has a bending magnet 31B of a sector type. In FIGS. 7A and 7B, the charged particle beam bent by the beam shielding magnet 34 propagates in a direction perpendicular to a bending plane of the bending magnet 31B. In this case, the charged particle beam is injected/extracted at an angle of 90 degrees with respect to the magnetic pole surface of the bending magnet 31B. FIG. 7A is a plan view of the beam interrupting device 700A when viewed from the top of the beam transport system 300. FIG. 7B is a front view of the beam interrupting device 700A when viewed from the side of the beam transport system 300. The charged particle beam receives a focusing force in the bending plane of the bending magnet 31B of the sector type. The charged particle beam, however, does not receive a focusing force acting in a direction perpendicular to the bending plane of the bending magnet 31B. Therefore, the charged particle beam bent at a bending angle and directed toward the direction perpendicular to the bending plane of the bending magnet 31B by the beam shielding magnet 34 propagates in the bending magnet 31B along the orbit 70 under the condition that the bending angle is maintained. In this case, the bending angle is formed between the direction of the propagation of the charged particle beam bent by the beam shielding magnet 34 and the center orbit 30 of the charged particle beam that is not bent by the beam shielding magnet 34. In FIGS. 7A and 7B, the charged particle beam receives a diverging force in the direction perpendicular to the bending plane from the quadrupole magnet 36, then propagates in the bending magnet 31B at a larger bending angle with respect to the center orbit 30 along the beam orbit 70, and is discarded by the beam dump 35.

The present embodiment offers the same effect as that obtained in the first embodiment.

According to the present embodiment, the charged particle beam bent by the beam shielding magnet 34 is further bent by the quadrupole magnet 36 and then propagates along the orbit 70. This can reduce required performance of the parts constituting the beam interrupting device 700A. Thus, the cost of manufacturing the beam interrupting device 700A can be reduced. In addition, the drift length of the straight section of the beam transport system 300 can be further reduced. Therefore, the size of the particle beam therapy system can be reduced. As a result, an irradiation beam suitable for the particle beam therapy using the spot scanning method can be achieved.

Third Embodiment

The entire configuration and operations of a particle beam therapy system 100B according to a third embodiment of the present invention are described below. In the third embodiment, only parts different from the first embodiment are described.

Figure 8:
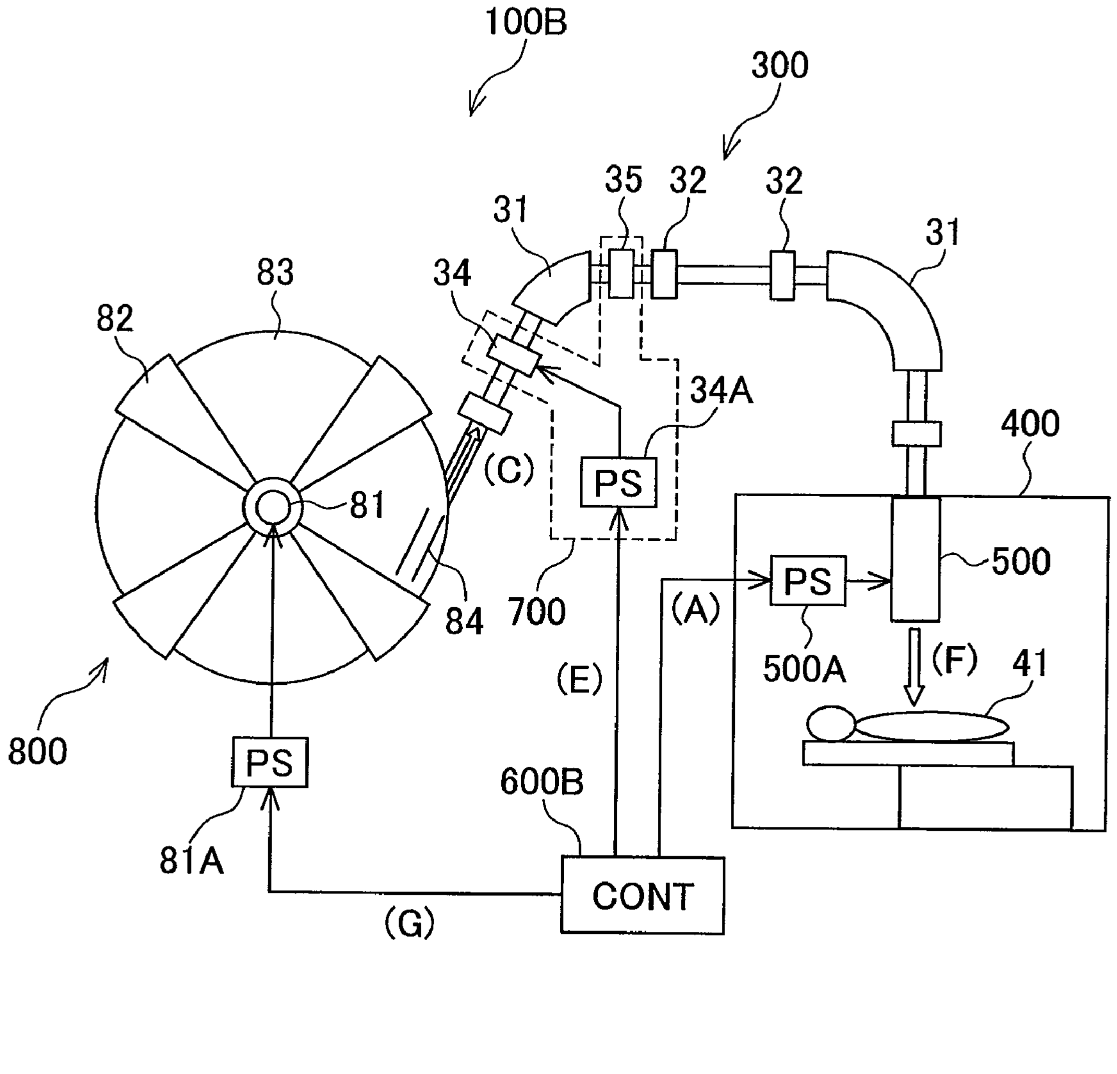
FIG. 8 is a diagram showing the configuration of a particle beam therapy system according to a third embodiment of the present invention.

FIG. 8 is a diagram showing the configuration of the particle beam therapy system 100B according to the third embodiment. The particle beam therapy system 100B according to the third embodiment uses a cyclotron 800 as an accelerator for accelerating a charged particle beam. The cyclotron 800 includes an ion source 81, an accelerating cavity 82, a bending magnet 83 and an extraction deflecting magnet 84. The ion source 81 is adapted to generate a charged particle beam. The accelerating cavity 82 is adapted to accelerate the charged particle beam for each circular movement of the beam. The bending magnet 83 is adapted to bend the charged particle beam to cause the beam to spirally circle around the cyclotron 800. The extraction deflecting magnet 84 is adapted to cause the charged particle beam to be extracted from the cyclotron 800 when the charged particle beam has a predetermined energy level. The cyclotron 800 turns on and off a high voltage (to be applied to the ion source 81) to turn on and off the beam that is to be extracted from the cyclotron 800. More specifically, one of the following voltages is turned on and off to turn on and off the beam that is to be extracted from the cyclotron 800: an arc voltage used to generate plasma that is a source of the charged particle beam; an acceleration voltage used to extract the charged particle beam from the plasma; and a deflecting voltage applied to the charged particle beam immediately after the extraction of the charged particle beam from the plasma. However, the charged particle beam that is to be extracted from the cyclotron 800 cannot be instantly turned on and off by turning on and off any one of the aforementioned voltages. The turning on and off of the beam are delayed due to a response of a high voltage power supply or due to the time of the circular movement of the charged particle beam circling around the cyclotron 800.

The particle beam therapy system 100B includes a controller 600B. The controller 600B is connected with a power supply 81A, a power supply 34A and a power supply 500A. The power supply 81A is provided for the ion source 81A included in the cyclotron 800. The power supply 34A is provided for the beam shielding magnet 34 included in the beam interrupting device 700. The power supply 500A is provided for the scanning magnets 51*a* and 51*b* included in the irradiation device 500. The controller 600B transmits a voltage control signal to the power supply 81A provided for the ion source 81 to control a voltage that is to be applied to the ion source 81.

Figures 9A, 9B, 9C, 9D, 9E:
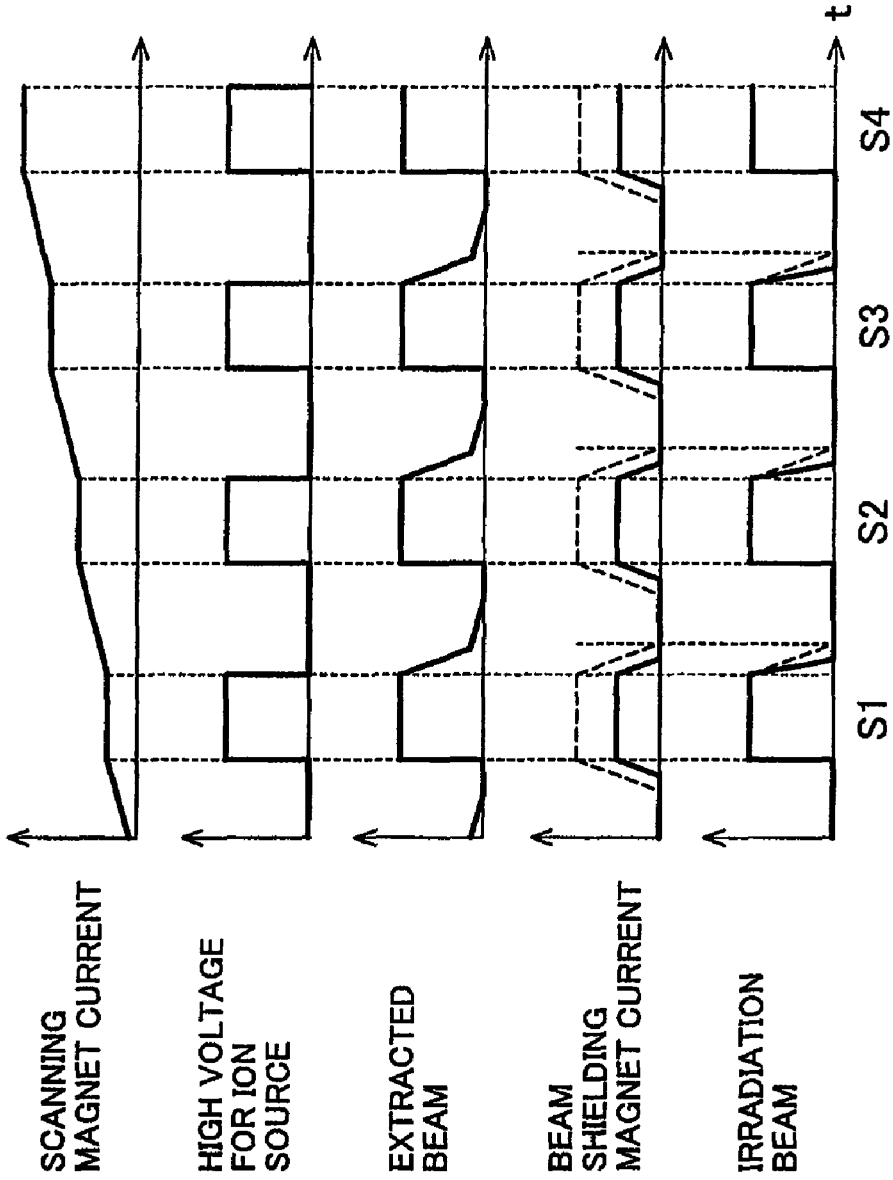
FIGS. 9A to 9E are timing charts of operations performed in accordance with a spot scanning method used in the particle beam therapy system according to the third embodiment.

FIGS. 9A to 9E are timing charts showing operations performed in accordance with a spot scanning method used in the particle beam therapy system 100B according to the third embodiment. In the first embodiment (FIGS. 4A to 4E), the RF power that is to be supplied to the extraction device 26 provided in the synchrotron 200 is turned on and off. In the third embodiment, however, the high voltage that is to be supplied to the ion source 81 provided in the cyclotron 800 is turned on and off as shown in FIG. 9B. In each of the first and third embodiments, it takes a certain time to block the charged particle beam extracted from the accelerator, so that an irradiation during the delay time (delay irradiation) occurs. In this embodiment, the configuration of the beam interrupting device 700 to reduce the delay irradiation dose of the beam to be extracted is the same as that of the beam interrupting device 700 according to the first embodiment. However, operations of the beam interrupting device 700 according to the third embodiment are different from those of the beam interrupting device 700 according to the first embodiment.

As shown in FIG. 9D, the irradiation beam can be turned on under the condition that the beam shielding magnet 34 is excited in the present embodiment. Therefore, the irradiation beam is turned off in a fail-safe manner when a failure occurs in a device of the beam interrupting device. Thus, the particle beam therapy system according to the present embodiment has higher security. Since the irradiation beam is turned on under the condition that the beam shielding magnet 34 is excited, the position of the bending magnet 31 (provided on the immediate downstream side of the beam shielding magnet 34) and the bending angle of the beam bent by the bending magnet 31 are determined in consideration of the bending angle of the beam bent by the beam shielding magnet 34. In the third embodiment, the same operations as those performed in the first embodiment can be performed. That is, the beam shielding magnet can be excited to turn off the irradiation beam. In FIGS. 9D and 9E, broken lines indicates values obtained from a conventional technique. According to the technique (indicated by solid lines in FIGS. 9D and 9E) of the present invention, as is the case with the first embodiment, the amount of the exciting current applied to the beam shielding magnet 34 and the time required for blocking the charged particle beam can be reduced.

The present embodiment offers the same effect as that obtained in the first embodiment.

Since the cyclotron is smaller than the synchrotron, the size of the particle beam therapy system according to the present embodiment can be reduced. On the other hand, when the size of the particle beam therapy system having the cyclotron is the same as the size of the particle beam therapy system having the synchrotron, the drift length of the straight section of the beam transport system 300 included in the particle beam therapy system according to the present embodiment can be larger than that of the straight section of the beam transport system 300 included in the particle beam therapy system according to the first embodiment. Thus, a distance (drift distance) between the bending magnet 31 and the beam dump 35 can be larger, and the required performance of the parts constituting the beam interrupting device 700 can be reduced.

Fourth Embodiment

Figure 10:
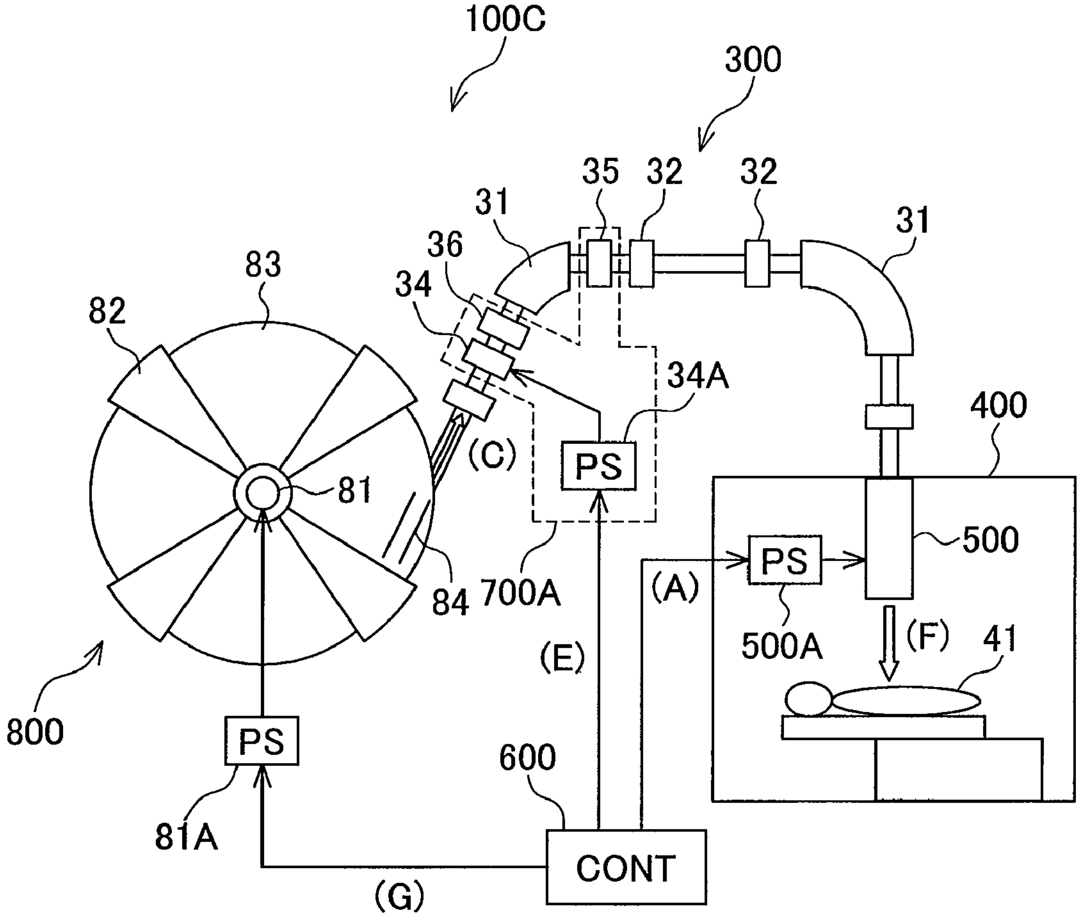
FIG. 10 is a diagram showing the configuration of a particle beam therapy system according to a fourth embodiment of the present invention.
Figure 11:
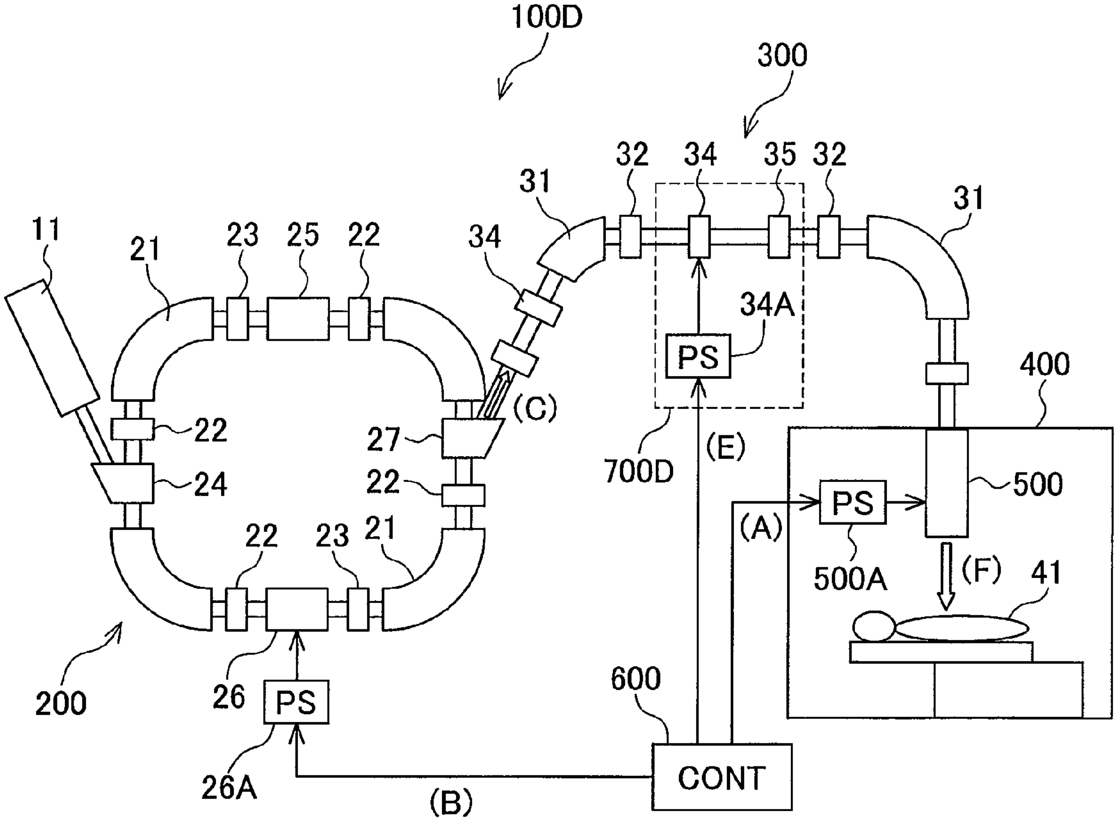
FIG. 11 is a diagram showing the configuration of a conventional particle beam therapy system.

Next, the configuration of a particle beam therapy system 100C according to a fourth embodiment of the present invention is described below. FIG. 10 is a diagram showing the configuration of the particle beam therapy system 100C according to the fourth embodiment.

In the fourth embodiment, the cyclotron 800 is used as an accelerator for accelerating a charged particle beam in the same manner as in the third embodiment. A beam interrupting device included in the particle beam therapy system 100C according to the fourth embodiment has the same configuration as that of the beam interrupting device 700A used in the second embodiment. In the fourth embodiment, as is the case with the second embodiment, the quadrupole magnet 36 is provided between the bending magnet 31 constituting a part of the beam transport system 300 and the beam shielding magnet 34 located on the inlet side of the bending magnet 31. The quadrupole magnet 36 is adapted to bend a charged particle beam bent by the beam shielding magnet 34. The beam dump 35 is provided on the outlet side of the bending magnet 31 and adapted to discard the bent charged particle beam. In the present embodiment, the required performance of the parts constituting the beam interrupting device can be reduced to the lowest performance compared with the first to third embodiments. In addition, the size of the entire particle beam therapy system can be reduced, and an irradiation beam suitable for a particle beam therapy using the spot scanning method can be achieved.

The present embodiment offers the same effect as that obtained in the second embodiment.

Since the cyclotron is smaller than the synchrotron, the size of the particle beam therapy system according to the present embodiment can be reduced. On the other hand, when the size of the particle beam therapy system having the cyclotron is the same as the size of the particle beam therapy system having the synchrotron, the drift length of the straight section of the beam transport system 300 included in the particle beam therapy system according to the present embodiment can be extended. Thus, the drift distance between the bending magnet 31 and the beam dump 35 can be extended, so that requested performance of the parts constituting the beam interrupting device 700 can be reduced.

As described in the first to fourth embodiments, the particle beam therapy system according to each of the first to fourth embodiments can achieve an irradiation beam suitable for the particle beam therapy using the spot scanning method, and can be constructed in a small size and with low cost. In addition, the particle beam therapy system according to each of the first to fourth embodiments can be easily adjusted and easily achieve high-accuracy therapy irradiation for a complicated affected area of a patient.

In addition to a particle beam therapy system used for a cancer treatment, this invention is applicable to a physical investigation in which a high-energy charged particle beam accelerated by accelerator such as a synchrotron or cyclotron needs to be irradiated on a target with high accuracy and with required strength distribution.

What is claimed is:

1. A particle beam therapy system comprising:

an accelerator for accelerating a charged particle beam such that the charged particle beam has a predetermined energy level to be extracted;

an irradiation device for irradiating an irradiation target with the charged particle beam;

a beam transport system having a bending magnet for introducing the charged particle beam which has been extracted from said accelerator into said irradiation device, the bending magnet bending the charged particle beam; and a beam interrupting device provided in the beam transport system and blocking supply of the charged particle beam to said irradiation device;

wherein said accelerator includes an extraction deflecting magnet for bending the charged particle beam accelerated to said predetermined energy level to extract the charged particle beam from said accelerator into said beam transport system, and wherein said beam interrupting device includes a beam shielding magnet and a beam dump, the beam shielding magnet being located on an upstream side of the bending magnet with respect to the direction of flow of the charged particle beam in said beam transport system and is for bending the charged particle beam extracted from said accelerator by said extraction deflecting magnet upon blocking the supply of the charged particle beam to said irradiation device, and the beam dump being located on a downstream side of the bending magnet with respect to the direction of the flow of the charged particle beam.

2. The particle beam therapy system according to claim 1, wherein said beam interrupting device has a quadrupole magnet provided between the bending magnet and the beam shielding magnet for bending the charged particle beam bent by the beam shielding magnet.

3. The particle beam therapy system according to claim 1, wherein the bending magnet is configured as a rectangular type having opposed end surfaces substantially parallel to each other, and the beam shielding magnet bends the charged particle beam to cause the charged particle beam to propagate in a bending plane of the bending magnet.

4. The particle beam therapy system according to claim 1, wherein the bending magnet is configured as a sector type, and the beam shielding magnet bends the charged particle beam to cause the charged particle beam to propagate in a direction perpendicular to a bending plane of the bending magnet.

5. The particle beam therapy system according to claim 1, further comprising a controller for transmitting an extraction stop control signal when the dose of the charged particle beam irradiated on the irradiation target reaches a set value, and controlling the beam shielding magnet such that the charged particle beam extracted from the accelerator after the transmission of the extraction control signal collides with the beam dump.

6. The particle beam therapy system according to claim 1, further comprising:

scanning magnets for changing the position of a spot of the charged particle beam on the irradiation target; and a controller for controlling the beam shielding magnet to cause the beam shielding magnet to block the supply of the charged particle beam to the irradiation device when the position of the spot of the charged particle beam is changed.

7. The particle beam therapy system according to claim 2, wherein the bending magnet is configured as a rectangular type having opposed end surfaces substantially parallel to each other, and the beam shielding magnet is adapted to bend the charged particle beam to cause the charged particle beam to propagate in a bending plane of the bending magnet.

8. The particle beam therapy system according to claim 2, wherein the bending magnet is configured as a sector type, and the beam shielding magnet is adapted to bend the charged particle beam to cause the charged particle beam to propagate in a direction perpendicular to a bending plane of the bending magnet.

9. The particle beam therapy system according to claim 2, further comprising a controller for transmitting an extraction stop control signal when the dose of the charged particle beam irradiated on the irradiation target reaches a set value, and controlling the beam shielding magnet such that the charged particle beam extracted from the accelerator after the transmission of the extraction control signal collides with the beam dump.

10. The particle beam therapy system according to claim 2, further comprising:

scanning magnets for changing the position of a spot of the charged particle beam on the irradiation target; and a controller for controlling the beam shielding magnet to cause the beam shielding magnet to block the supply of the charged particle beam to the irradiation device when the position of the spot of the charged particle beam is changed.

11. A particle beam therapy system comprising:

an accelerator for accelerating a charged particle beam such that the charged particle beam has a predetermined energy level to be extracted;

an irradiation device for irradiating an irradiation target with the charged particle beam;

a beam transport system having a bending magnet for introducing the charged particle beam extracted from said accelerator into said irradiation device, the bending magnet being adapted to bend the charged particle beam; and a beam interrupting device provided in the beam transport system and blocking supply of the charged particle beam to said irradiation device;

wherein said beam interrupting device includes a beam shielding magnet and a beam dump, the beam shielding magnet being located on an upstream side of the bending magnet with respect to the direction of flow of the charged particle beam, and the beam dump being located in the bending magnet, and wherein said beam interrupting device has a quadrupole magnet provided between the bending magnet and the beam shielding magnet and adapted to bend the charged particle beam by the beam shielding magnet.

* * * * *